(12) United States Patent
Hasegawa et al.

(10) Patent No.: US 8,545,807 B2
(45) Date of Patent: Oct. 1, 2013

(54) NEAR INFRARED HIGH EMISSION RARE-EARTH COMPLEX

(75) Inventors: Yasuchika Hasegawa, Sapporo (JP); Hideki Kawai, Hamamatsu (JP); Tsuyoshi Kawai, Ikoma (JP)

(73) Assignees: National University Corporation Nara Institute of Science and Technology, Ikoma-shi (JP); National University Corporation Shizuoka University, Shizuoka-shi (JP)

( * ) Notice: Subject to any disclaimer, the term of this patent is extended or adjusted under 35 U.S.C. 154(b) by 242 days.

(21) Appl. No.: 12/920,244

(22) PCT Filed: Feb. 26, 2009

(86) PCT No.: PCT/JP2009/000866
§ 371 (c)(1),
(2), (4) Date: Aug. 30, 2010

(87) PCT Pub. No.: WO2009/110199
PCT Pub. Date: Sep. 11, 2009

(65) Prior Publication Data
US 2011/0003979 A1    Jan. 6, 2011

(30) Foreign Application Priority Data

Mar. 4, 2008  (JP) ................................. 2008-052779

(51) Int. Cl.
*A61K 51/00* (2006.01)
*A61M 36/14* (2006.01)
(52) U.S. Cl.
USPC ........................................ 424/1.11; 424/1.77
(58) Field of Classification Search
USPC ....................................................... 424/1.11
See application file for complete search history.

(56) References Cited

U.S. PATENT DOCUMENTS 7,250,117 B2 * 7/2007 Iwanaga et al. .......... 252/301.16

FOREIGN PATENT DOCUMENTS

| JP | A-2000-086952 | 3/2000 |
| JP | A-2005-082529 | 3/2005 |
| JP | A-2005-114909 | 4/2005 |

OTHER PUBLICATIONS

Supplementary European Search Report dated Apr. 14, 2011 for European Patent Application No. EP 09 71 8512.
J. Phys. Chem, A 2007, American Chemical Society, Enhanced Lasing Properties of Dissymmetric Eu(III) Complex with Bidentate Phosphine Ligands, Kazuki Nakamura et al., pp. 3029-3037.
Nakamura et al., "Improvement of lasing properties of europium (III) complexes by increase of emission quantum yield," Thin Solid Films, 2008, vol. 516, pp. 2376-2381.
Hasegawa et al., "Luminescence of Novel Neodymium Sulfonylaminate Complexes in Organic Media," *Angew. Chem. Int. Ed.*, 2000, vol. 39, No. 2, pp. 357-360.
Puntus et al., "Intense Near-Infrared Luminescence of a Mesomorphic Ionic Liquid Doped with Lanthanide β-Diketonate Ternary Complexes," *Eur. J. Inorg. Chem.*, 2005, pp. 4739-4744.
Hasegawa et al., "Photosensitized Near-Infrared Luminescence of Yb(III) Complexes Containing Phenanthroline Derivatives," *Japanese Journal of Applied Physics*, 2008, vol. 47, No. 2, pp. 1192-1195.
Written Opinion of the International Searching Authority in International Application No. PCT/JP2009/000866; dated Mar. 31, 2009 (with English-language translation).
International Preliminary Report on Patentability in International Application No. PCT/JP2009/000866; dated Oct. 12, 2010 (with English-language translation).
International Search Report in International Application No. PCT/JP2009/000866; dated Mar. 31, 2009 (with English-language translation).
Nov. 27, 2012 Office Action issued in Japanese Patent Application No. 2010-501786 (with English Translation).
Office Action issued in European Patent Application No. 09 718 512.8 dated May 3, 2012.

* cited by examiner

*Primary Examiner* — Michael G Hartley
*Assistant Examiner* — Melissa Perreira
(74) *Attorney, Agent, or Firm* — Oliff & Berridge, PLC

(57) ABSTRACT

The present invention has been created to provide a near infrared high emission rare-earth complex having an excellent light-emitting property in the near infrared region. The near infrared high emission rare-earth complex of the present invention is characterized in that its structure is expressed by the following general formula (1):

(1)

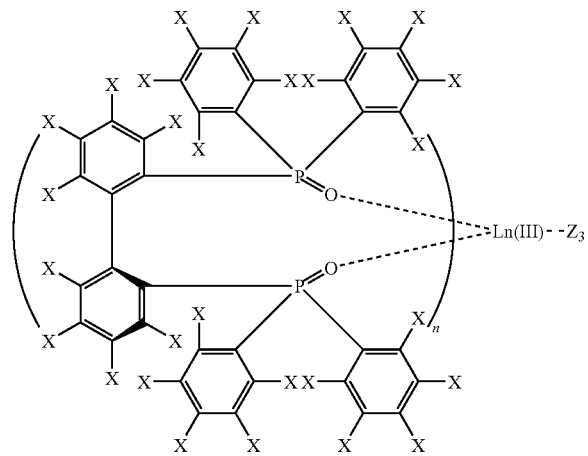

where Ln(III) represents a trivalent rare-earth ion; n is an integer equal to or greater than three; Xs represent either the same member or different members selected from a hydrogen atom, a deuterium atom, halogen atoms, $C_1$-$C_{20}$ groups, hydroxyl groups, nitro groups, amino groups, sulfonyl groups, cyano groups, silyl groups, phosphonic groups, diazo groups and mercapto groups; and Z represents a bidentate ligand.

4 Claims, 2 Drawing Sheets

| | RARE-EARTH COMPLEX | EMISSION QUANTUM YIELD (%) |
|---|---|---|
| PRODUCT EXAMPLE 1 | Yb(PMS)$_3$(BIPHEPO)$_3$ | 53.0% |
| COMPARATIVE EXAMPLE 1 | Yb(CH$_3$COO)$_3$ | 1.5% |
| COMPARATIVE EXAMPLE 2 | Yb(PMS)$_3$(H$_2$O)$_n$ | 5.3% |

NEAR INFRARED HIGH EMISSION RARE-EARTH COMPLEX

TECHNICAL FIELD

The present invention relates to a near infrared high emission rare-earth complex that emits light in the near infrared region when irradiated with a predetermined excitation light.

BACKGROUND ART

Various kinds of rare-earth complexes have conventionally been developed as optical functional materials or luminescent materials. Among those complexes, a rare-earth complex that emits light in the near infrared region is particularly expected to be used in security-related areas due to its invisibility. It is also expected to be useful as a labeling agent used in bio-related areas because it can efficiently permeate into biological bodies. Furthermore, the near infrared light has high utility values in the field of optical information communications.

The present inventor and their colleagues have found that a composition containing a rare-earth complex with a +3 valence has an excellent light-emitting property. Particularly, they developed a high emission neodymium complex as a luminescent material that exhibits an excellent light-emitting property in the near infrared region (Non-Patent Document 1). This neodymium complex has an emission quantum yield of approximately 3% in an organic medium in the near infrared region.

Bunzli et al. in Switzerland announced the creation of an ytterbium complex having an emission quantum yield of 2.1% in the near infrared region (Non-Patent Document 2). In recent years, the present inventors have also created an ytterbium complex having an emission quantum yield of approximately 7.4% in the near infrared region (Non-Patent Document 3).

Non-Patent Document 1: Y. Hasegawa et al., Angew. Chem. Int. Ed., 39,357 (2000)
Non-Patent Document 2: J. G. Bunzli et al., Eur. J. Inorg. Chem., 23, 4739 (2005)
Non-Patent Document 3: Y. Hasegawa et al., 2007 Fall Meeting of the Chemical Society of Japan, Jpn. J. Appl. Phys. in press

DISCLOSURE OF THE INVENTION

Problem to be Solved by the Invention

Thus, various kinds of rare-earth complexes that emit light in the near infrared region have been previously developed. However, these previous products have low emission quantum yields and have not achieved satisfactory levels of light-emitting properties. Therefore, these complexes need to be used in large quantity to obtain adequate emission intensity for optical functional materials.

The problem to be solved by the present invention is to provide a near infrared high emission rare-earth complex having an excellent light-emitting property in the near infrared region.

Means for Solving the Problems

If the molecular design is performed so that a low vibration structure is created to reduce the molecular vibration of the complex, the deactivation of excited electrons due to the molecular vibration will be suppressed and the emission quantum yield will improve. Taking this into account, the present inventors have continued research on a rare-earth complex with which a high level of emission quantum yield can be attained in the near infrared region.

As a result, it has been found that a ternary rare-earth complex with three or more bidentate phosphine oxide ligands having a biphenyl base and three bidentate ligands which differ from the aforementioned ligands, has an emission quantum yield significantly higher than those of the well-known near infrared emission rare-earth complexes. Thus, the present invention has been completed. In the present specification, such a rare-earth complex is referred to as a near infrared high emission rare-earth complex.

The phosphate double bond is known as a low vibration structure. It seems that the coordination of a ligand having such a structure suppresses the deactivation of electrons and thereby improves the emission quantum yield in the rare-earth complex of the present invention.

Particularly, the present invention pertains to a near infrared high emission rare-earth complex expressed by the following general formula (1):

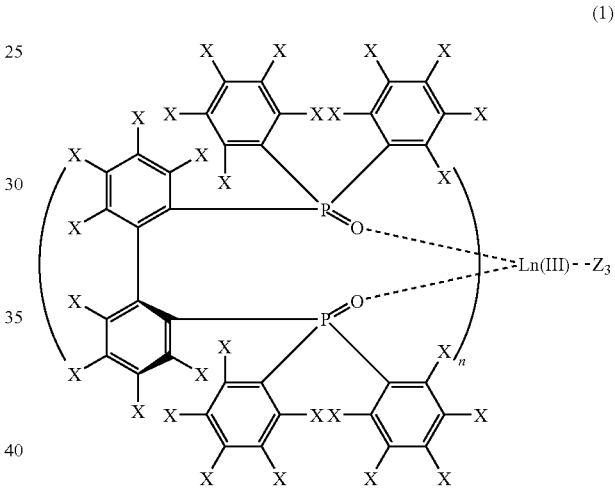

(1)

where Ln(III) represents a trivalent rare-earth ion; n is an integer equal to or greater than three; Xs represent either the same member or different members selected from a hydrogen atom, a deuterium atom, halogen atoms, $C_1$-$C_{20}$ groups, hydroxyl groups, nitro groups, amino groups, sulfonyl groups, cyano groups, silyl groups, phosphoric groups, diazo groups and mercapto groups; and Z represents a bidentate ligand.

The present invention also pertains to a near infrared high emission rare-earth complex in which the ligand represented by Z in the general formula (1) is expressed by the following general formula (2):

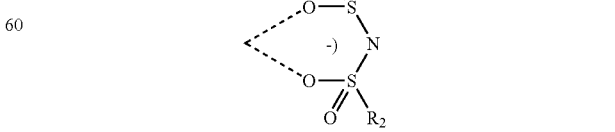

(2)

where $R_1$ and $R_2$ are the same member or different members selected from $C_1$-$C_{22}$ aliphatic groups free of hydrogen atoms, aromatic groups free of hydrogen atoms, and aromatic heterocyclic groups free of hydrogen atoms.

$Yb^{3+}$, $Er^{3+}$ and $Nd^{3+}$ exhibit excellent light-emitting properties in the near infrared region. Accordingly, it is possible to use $Yb^{3+}$, $Er^{3+}$ and $Nd^{3+}$ as the central ion of the near infrared high emission rare-earth complex of the present invention.

Effect of the Invention

The near infrared high emission rare-earth complex according to the present invention exhibits a high level of emission quantum yield in the near infrared region and hence is useful for applications in the areas related to security, biological and medical technologies, and optical information communications. For example, it can be used in security inks, bio-labeling agents, medical lasers and optical fibers.

BEST MODE FOR CARRYING OUT THE INVENTION

The present invention is hereinafter described in detail based on the production examples and product examples.

Production Example 1

Synthesis of Complex $Yb(PMS)_3(H_2O)_8$

Ytterbium oxide ($Yb_2O_3$: 7.0 g, 17.8 mmol) was dispersed in 200 ml of water, and bistrifluoromethane sulfonylimide ($CF_3SO_2NHSO_2CF_3$(PMS): 10.0 g, 35.6 mmol) was added to it. The liquid was stirred for 120 hours at room temperature, and subsequently filtered to remove unreacted $Yb_2O_3$. Finally, water was distilled away from the filtrate to obtain a white solid, which was the objective compound. The yield was 10.9 g. The result of an elementary analysis of the obtained complex $Yb(PMS)_3(H_2O)_8$ is shown below.

Elementary analysis: C6H16F18O20S6Yb
Measured values: C, 6.06; H, 1.19; N, 3.63%
Calculated values: C, 6.23; H, 1.39; N, 3.63%

Production Example 2

Synthesis of 1,1'-biphenyl-2,2'-diylbisdiphenylphosphineoxide 1,1'-biphenyl-2,2'-diylbisdiphenylphosphineoxide $((C_6H_5)_2P(C_6H_4)-(C_6H_4)P(C_6H_5)_2$ (BIPHEP) 1.0 g) was dissolved in 60 ml of dichloromethane, into which 5 ml of 30% hydrogen peroxide water was dropped in ice bath, and the solution was stirred for 6 hours. The obtained reaction solution was washed with water several times, and the dichloromethane layer was dried by means of magnesium sulfate. Subsequently, magnesium sulfate was removed by filtration, and dichloromethane was distilled away from the obtained solution to obtain a white solid. Then, this white solid was re-crystallized with water/ethanol to obtain the objective compound. The result of an $^1$H-NMR measurement (acetone-$d_6$, standard reference material TMS; ppm) is shown below.

$^1$H-NMR (acetone-$d_6$, standard reference material TMS; ppm): δ7.7, 7.55, 7.4, 7.2, 6.9 (m, aromatic C—H)

Product Example 1

Synthesis of Complex $Yb(PMS)_3(BIPHEPO)_3$

Figure 1:
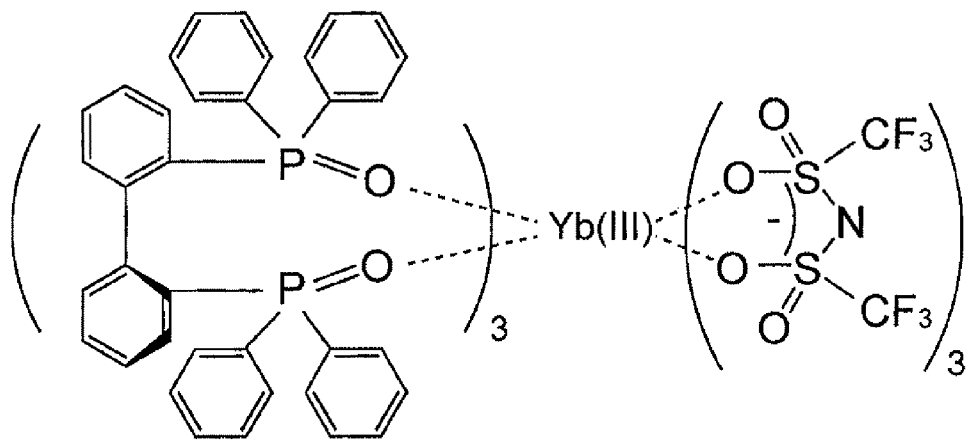
FIG. 1 is a diagram showing the chemical formula of a complex $Yb(PMS)_3(BIPHEPO)_3$, which is the first example of the present invention.

The Yb complex ($Yb(PMS)_3(H_2O)_8$: 0.13 g, 0.12 mmol) and 1,1'-biphenyl-2,2'-diylbisdiphenylphosphineoxide (BIPHEPO: 0.2 g, 0.36 mmol) obtained by the previously described method were dissolved in 100 ml of methanol and heated to reflux for 12 hours. Twelve hours later, impurities were removed by filtration, and methanol was removed by vacuum evaporation to obtain a white product. After this powder was dispersed in water to remove the unreacted remnant of the complex $Yb(PMS)_3(H_2O)_8$, the filtration and vacuum-drying processes were successively performed to obtain a white objective compound. The yield was 92 mg in weight and 28% in percentage. The results of an IR measurement ($cm^{-1}$), $^1$H-NMR measurement (acetone-$d_6$, standard reference material TMS; ppm) and elementary analysis of the obtained complex $Yb(PMS)_3(BIPHEPO)_3$ are shown below. Additionally, the chemical formula of the complex $Yb(PMS)_3(BIPHEPO)_3$ is shown in FIG. 1.

IR($cm^{-1}$): 1645 (C=C, st), 1439, 1352 (S=O, st), 1190, 1134, 1055 (P=O, C—F, C—N, st)

$^1$H-NMR (acetone-$d_6$, standard reference material TMS; ppm): δ7.5, 7.3 (m, aromatic C—H)

Elementary analysis: C114H84F18N3O18P6S6Yb
Measured values: C, 50.98; H, 3.09; N, 1.59%
Calculated values: C, 51.14; H, 3.16; N, 1.57%

[Emission Quantum Yield and Emission Spectrum]

The emission quantum yield and emission spectrum of a dimethylsulfoxide-$d_6$ solution of the complex $Yb(PMS)_3(BIPHEPO)_3$ obtained in Product Example 1 (Yb ion concentration: 10 mM) were measured (excitation wavelength: 940 nm). Additionally, the emission quantum yield and emission spectrum of two Yb complexes, $Yb(CH_3COO)_3$ and $Yb(PMS)_3(H_2O)_n$ (n=1 to 10), were measured as comparative examples under the same conditions as in the case of the complex $Yb(PMS)_3(BIPHEPO)_3$. $Yb(CH_3COO)_3$ is a standard complex and a marketed product of this complex was used in the measurement. The emission quantum yield is expressed as a relative percentage calculated on the assumption that the emission quantum yield of $Yb(CH_3COO)_3$ is 1.5%. The measured results are shown in FIGS. 2 and 3.

[Absorption Spectrum]

The absorption spectrum of a dimethylsulfoxide-$d_6$ solution of the complex $Yb(PMS)_3(BIPHEPO)_3$ of Product Example 1 (Yb ion concentration: 10 mM) was measured with an ultraviolet-visible near-infrared transmission spectrophotometer. The result is shown in FIG. 4.

Figure 2:
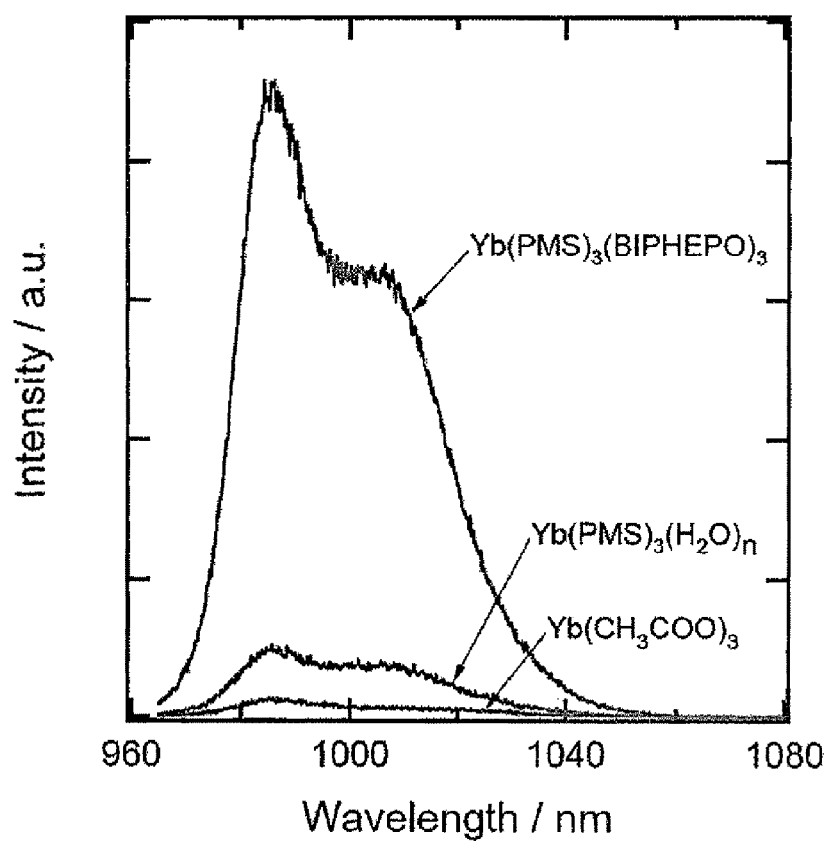
FIG. 2 is a graph showing the emission spectra of the complex $Yb(PMS)_3(BIPHEPO)_3$ and two other Yb complexes ($Yb(CH_3COO)_3$, $Yb(PMS)_3(H_2O)_n$) as comparative examples.
Figures 3, 4:
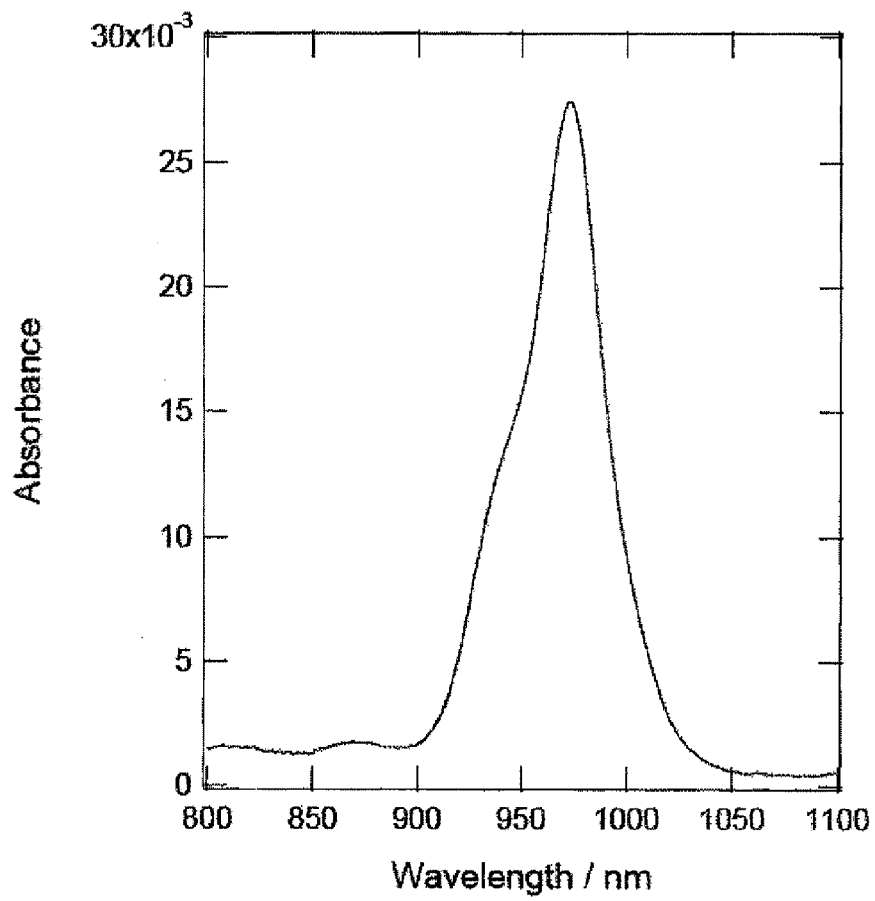
FIG. 3 is a table showing the emission quantum yields of the complex $Yb(PMS)_3(BIPHEPO)_3$ and the other Yb complexes ($Yb(CH_3COO)_3$, $Yb(PMS)_3(H_2O)_n$) as the comparative examples.
FIG. 4 is a graph showing the absorption spectrum of the complex $Yb(PMS)_3(BIPHEPO)_3$.

As is evident from FIGS. 2 and 3, the complex $Yb(PMS)_3(BIPHEPO)_3$ of Product Example 1 had a strong emission of light in the near infrared region (around 980 nm). Its emission quantum yield was beyond expectation and significantly exceeded those of the comparative examples. Furthermore, the emission quantum yield is drastically higher than those of the ytterbium complexes and neodymium complex disclosed in Non-Patent Documents 1-3 mentioned in the "BACKGROUND ART" section.

Thus, the rare-earth complex of Product Example 1 exhibits an excellent light-emitting property in the near infrared region and hence can produce an adequately strong emission of light even in small quantity. Such a material is useful in security-related areas (e.g. security inks) and bio-related areas (e.g. biological body markers).

As shown in FIG. 4, the complex $Yb(PMS)_3(BIPHEPO)_3$ has a broad absorption peak over a range from 900 to 1050 nm due to the f-f transition of the central ion, $Yb^{3+}$. Such an absorption property will probably have considerable effects when the complex $Yb(PMS)_3(BIPHEPO)_3$ is combined with an electroluminescence (EL) or similar broad light-emitting element.

Other than ytterbium (Yb), erbium (Er) and neodymium (Nd) are also known as rare-earth elements having an emission spectrum line in the near infrared region. Therefore, it is expected that similar effects will be obtained even if $Er^{3+}$ or $Nd^{3+}$ is used in place of $Yb^{3+}$ as the central ion of the near infrared high emission rare-earth complex of the present invention. Examples of the synthesizing method for a rare-earth complex of the present invention using $Er^{3+}$ or $Nd^{3+}$ are hereinafter described.

Product Example 2

Synthesis of Complex $Nd(PMS)_3(BIPHEPO)_3$

An Nd complex ($Nd(PMS)_3(H_2O)_8$: 0.31 g, 0.3 mmol), which was obtained by a synthesizing method similar to the method used for the aforementioned Yb complex, and 1,1'-biphenyl-2,2'-diylbisdiphenylphosphineoxide (BIPHEPO: 0.5 g, 0.9 mmol) were dissolved in 100 ml of methanol and heated to reflux for 12 hours. Twelve hours later, impurities were removed by filtration, and methanol was removed by vacuum distillation to obtain a pale purple product.

After this powder was dispersed in water to remove the unreacted remnant of the complex $Nd(PMS)_3(H_2O)_8$, the filtration and vacuum-drying processes were successively performed to obtain a pale purple objective compound. The yield was 230 mg in weight and 29% in percentage. The results of an IR measurement ($cm^{-1}$), $^1H$-NMR measurement (acetone-$d_6$, standard reference material TMS; ppm) and elementary analysis of the obtained complex $Nd(PMS)_3(BIPHEPO)_3$ are shown below.

IR($cm^{-1}$): 1635 (C=C, st), 1352 (S=O, st), 1192, 1142, 1053 (P=O, C—F, C—N, st)

$^1H$-NMR (acetone-$d_6$, standard reference material TMS; ppm): δ7.5, 7.2 (m, aromatic C—H)

Elementary analysis: C114H84F18N3NdO18P6S6
Measured values: C, 51.69; H, 3.13; N, 1.48%
Calculated values: C, 51.70; H, 3.20; N, 1.59%

Product Example 3

Synthesis of Complex $Er(PMS)_3(BIPHEPO)_3$

An Er complex ($Er(PMS)_3(H_2O)_8$: 0.31 g, 0.3 mmol), which was obtained by a synthesizing method similar to the method used for the aforementioned Yb complex, and 1,1'-biphenyl-2,2'-diylbisdiphenylphosphineoxide (BIPHEPO: 0.5 g, 0.9 mmol) were dissolved in 100 ml of methanol and heated to reflux for 12 hours. Twelve hours later, impurities were removed by filtration, and methanol was removed by vacuum distillation, and then by azeotropic distillation with hexane added thereto. As a result, a pink product was obtained.

After this powder was dispersed in water to remove the unreacted remnant of the complex $Er(PMS)_3(H_2O)_8$, the filtration and vacuum-drying processes were successively performed to obtain a pink objective compound. The yield was 12 mg in weight and 1.5% in percentage. The results of an IR measurement ($cm^{-1}$), $^1H$-NMR measurement (acetone-$d_6$, standard reference material TMS; ppm) and elementary analysis of the obtained complex $Er(PMS)_3(BIPHEPO)_3$ are shown below.

IR($cm^{-1}$): 1628 (C=C, st), 1350 (S=O, st), 1182, 1136, 1053 (P=O, C—F, C—N, st)

$^1H$-NMR (acetone-$d_6$, standard reference material TMS; ppm): δ7.5, 7.4 (m, aromatic C—H)

Elementary analysis: C114ErH84F18N3O18P6S6
Measure values: C, 50.89; H, 3.02; N, 1.42%
Calculated values: C, 51.26; H, 3.17; N, 1.57%

The invention claimed is:

1. A near infrared high emission rare-earth complex, comprising three bidentate phosphine oxide ligands having a biphenyl base and three bidentate ligands which differ from the aforementioned ligands, wherein the complex has a structure expressed by a following general formula (1):

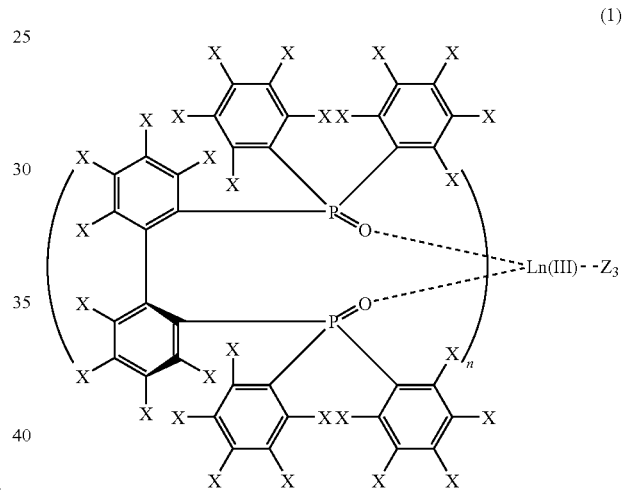

(1)

where Ln is Yb; n is three; Xs represent either a same member or different members selected from a hydrogen atom, a deuterium atom, halogen atoms, $C_1$-$C_{20}$ groups, hydroxyl groups, nitro groups, amino groups, sulfonyl groups, cyano groups, silyl groups, phosphonic groups, diazo groups and mercapto groups; and Z represents a bidentate ligand expressed by a general formula (2):

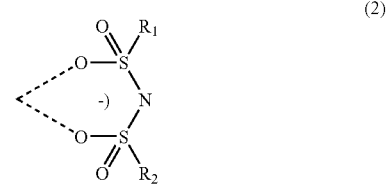

(2)

where $R_1$ and $R_2$ are a same member or different members selected from $C_1$-$C_{22}$ aliphatic groups free of hydrogen atoms, aromatic groups free of hydrogen atoms, and aromatic heterocyclic groups free of hydrogen atoms.

2. A security ink using a near infrared high emission rare-earth complex comprising three bidentate phosphine oxide ligands having a biphenyl base and three bidentate ligands which differ from the aforementioned ligands, wherein the complex has a structure expressed by a following general formula (1):

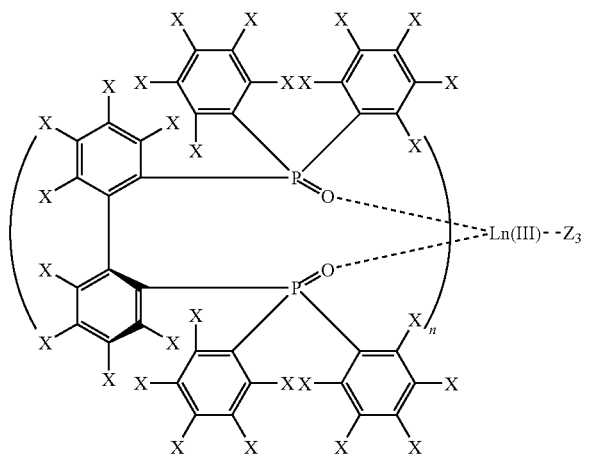

where Ln is Yb; n is three; Xs represent either a same member or different members selected from a hydrogen atom, a deuterium atom, halogen atoms, $C_1$-$C_{20}$ groups, hydroxyl groups, nitro groups, amino groups, sulfonyl groups, cyano groups, silyl groups, phosphonic groups, diazo groups and mercapto groups; and Z represents a bidentate ligand expressed by a general formula (2):

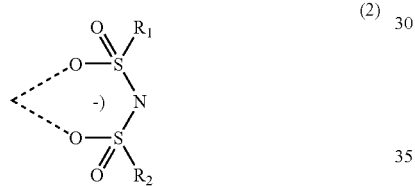

where $R_1$ and $R_2$ are a same member or different members selected from $C_1$-$C_{22}$ aliphatic groups free of hydrogen atoms, aromatic groups free of hydrogen atoms, and aromatic heterocyclic groups free of hydrogen atoms.

3. A light-emitting source using a near infrared high emission rare-earth complex comprising three bidentate phosphine oxide ligands having a biphenyl base and three bidentate ligands which differ from the aforementioned ligands, wherein the complex has a structure expressed by a following general formula (1):

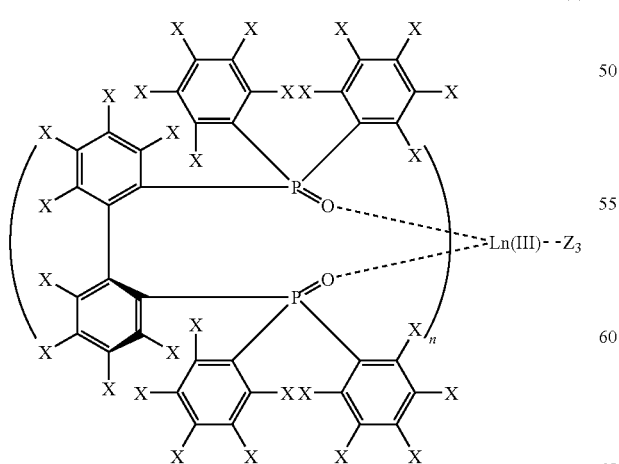

where Ln is Yb; n is three; Xs represent either a same member or different members selected from a hydrogen atom, a deuterium atom, halogen atoms, $C_1$-$C_{20}$ groups, hydroxyl groups, nitro groups, amino groups, sulfonyl groups, cyano groups, silyl groups, phosphonic groups, diazo groups and mercapto groups; and Z represents a bidentate ligand expressed by a general formula (2):

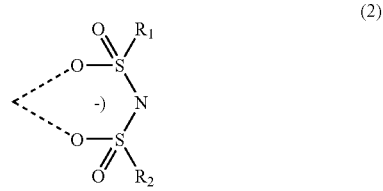

where $R_1$ and $R_2$ are a same member or different members selected from $C_1$-$C_{22}$ aliphatic groups free of hydrogen atoms, aromatic groups free of hydrogen atoms, and aromatic heterocyclic groups free of hydrogen atoms.

4. A labeling agent for a measurement, using a near infrared high emission rare-earth complex comprising three bidentate phosphine oxide ligands having a biphenyl base and three bidentate ligands which differ from the aforementioned ligands, wherein the complex has a structure expressed by a following general formula (1):

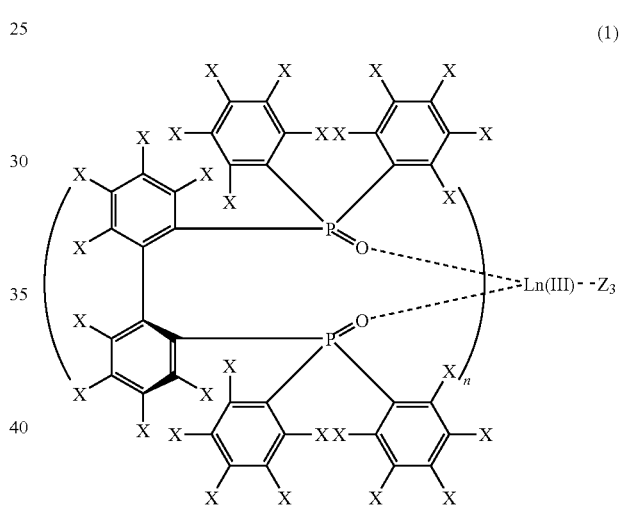

where Ln is Yb; n is three; Xs represent either a same member or different members selected from a hydrogen atom, a deuterium atom, halogen atoms, $C_1$-$C_{20}$ groups, hydroxyl groups, nitro groups, amino groups, sulfonyl groups, cyano groups, silyl groups, phosphonic groups, diazo groups and mercapto groups; and Z represents a bidentate ligand expressed by a general formula (2):

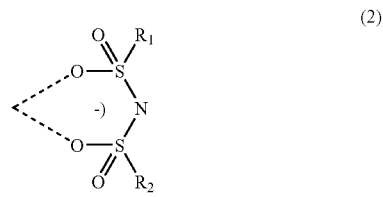

where $R_1$ and $R_2$ are a same member or different members selected from $C_1$-$C_{22}$ aliphatic groups free of hydrogen atoms, aromatic groups free of hydrogen atoms, and aromatic heterocyclic groups free of hydrogen atoms.

* * * * *